US008658699B2

(12) United States Patent
Kohane et al.

(10) Patent No.: US 8,658,699 B2
(45) **Date of Patent: *Feb. 25, 2014**

(54) CHEMICAL PERMEATION ENHANCERS ENHANCE NERVE BLOCKADE BY TOXINS

(75) Inventors: Daniel S. Kohane, Newton, MA (US); Itay Sagie, Haifa (IL); Emmanuel J. Simons, Somerville, MA (US)

(73) Assignees: Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/993,759

(22) PCT Filed: May 19, 2009

(86) PCT No.: PCT/US2009/044548

§ 371 (c)(1),
(2), (4) Date: Feb. 7, 2011

(87) PCT Pub. No.: WO2009/143174

PCT Pub. Date: Nov. 26, 2009

(65) Prior Publication Data

US 2011/0237611 A1 Sep. 29, 2011

Related U.S. Application Data

(60) Provisional application No. 61/054,398, filed on May 19, 2008.

(51) Int. Cl.

| | |
|---|---|
| ***A01N 37/18*** | (2006.01) |
| ***A61K 31/16*** | (2006.01) |
| ***C07D 471/04*** | (2006.01) |
| ***C07D 471/22*** | (2006.01) |
| ***C07D 487/04*** | (2006.01) |

(52) U.S. Cl.
USPC .......................................... 514/626; 514/257

(58) Field of Classification Search
USPC .......................................................... 514/626
See application file for complete search history.

(56) References Cited

U.S. PATENT DOCUMENTS

| | | | | |
|---|---|---|---|---|
| 4,029,794 | A * | 6/1977 | Adams et al. | 514/267 |
| 4,537,776 | A | 8/1985 | Cooper | |
| 4,820,720 | A | 4/1989 | Sanders | |
| 4,863,970 | A | 9/1989 | Patel | |
| 4,973,468 | A | 11/1990 | Chiang | |
| 5,006,342 | A | 4/1991 | Cleary | |
| 5,618,563 | A | 4/1997 | Berde | |
| 5,700,485 | A | 12/1997 | Berde | |
| 5,716,637 | A | 2/1998 | Anselem | |
| 6,326,020 | B1 * | 12/2001 | Kohane et al. | 424/426 |
| 6,455,066 | B1 | 9/2002 | Fischer | |
| 6,673,363 | B2 | 1/2004 | Luo | |

FOREIGN PATENT DOCUMENTS

| | | |
|---|---|---|
| EP | 0043738 | 9/1982 |
| WO | 9311798 | 6/1993 |
| WO | 0141550 | 6/2001 |
| WO | 0241915 | 5/2002 |
| WO | 2006034624 | 4/2006 |
| WO | WO 2006034624 A1 * | 4/2006 |
| WO | 2009143174 | 11/2009 |
| WO | 2009143175 | 11/2009 |

OTHER PUBLICATIONS

Ackerman, et al., "Penetration enhancers and othe factors governing percutaneous local anaesthesia with lidocaine", Acta Pharma. Et toxicological, 45 (1):58-65 (1979).

Adjei and Garren, "Pulmonary delivery of peptide drugs: effect of particle size on bioavailability of leuprolide acetate in healthy male volunteers", J Pharm. Res, 7:565-9 (1990).

Barnet, et al., "Site 1 sodium channel blockers prolong the duration of sciatic nerve blockade from tricyclic antidepressants", Pain 110:432-8 (2004).

Benoit, et al., "Pharmacologic correlation between local anesthetic-induced myotoxicity and disturbances of intracellular calcium distribution", Toxicol. Appl. Pharmacol., 52:187-198 (1980).

Bernards and Hill, "Physical and chemical properties of drug molecules governing their diffusion through the spinal meninges", Anesthesiology 77 (4):750-6 (1992).

Epstein-Barash, et al., "Prolonged duration local anesthesia with minimal toxicity", PNAS, 106(17):7125-30 (2009).

Fang, et al., "Synergistically enhanced transdermal prrmration and tropical analgesia of tetracaine gel containing menthol and ethanol in experimental and clinical studies", Eu J Pharm and Biopharm., 68:735-40 (2008).

(Continued)

*Primary Examiner* — Layla Soroush
(74) *Attorney, Agent, or Firm* — Pabst Patent Group LLP

(57) ABSTRACT

Chemical permeation enhancers (CPEs) improve access of local anesthetics to the nerve, thereby improving their performance. Surfactants, representing three CPE sub-groups: anionic, cationic, and nonionic surfactants, were co-injected with tetrodotoxin (TTX) or bupivacaine at the sciatic nerve of Sprague-Dawley rats. All enhancers produced marked concentration-dependent improvements in the frequency and duration of block with TTX but not bupivacaine. An in vitro toxicity assay showed a wide range of CPE myotoxicity, but in vivo histological assessment showed no signs of muscle or nerve damage at concentrations of CPEs that produced a half-maximal increase in the duration of block of TTX. There was no systematic relationship between the enhancers' charge or hydrophobicity and their enhancement of block duration or potency. Thus, CPEs can provide marked prolongation of nerve blockade from TTX, without apparent local tissue toxicity, and therefore enhance the clinical applicability of TTX for prolonged-duration local anesthesia.

23 Claims, 3 Drawing Sheets

(56) References Cited

OTHER PUBLICATIONS

Kohane, et al., "A re-examination of tetrodotoxin for prolonged duration local anesthesia", Anesthesiology, 89:119-31 (1998).
Kohane, et al., "Effects of adrenergic agonists and antagonists on tetrodotoxin-induced nerve block", Reg Anesth Pain Med, 26:239-45 (2001).
Kohane, et al., "Prolonged duration local anesthesia from tetrodotoxin-enhanced local anesthetic microspheres", Pain,104(1-2):415-21 (2003).
Kohane, et al., "Sciatic nerve blockade in infant, adolescent, and adult rats: a comparison of ropivacaine with bupivacaine", Anesthesiology, 89:1199-1208 (1998).
Kohane, et al., "The local anesthetic properties and toxicity of saxitonin homologues for rat sciatic nerve block in vivo", Reg Anesth Pain Med., 25:52-9 (2000).
Kohane, et al., "Vanilloid receptor agonists potentiate the in vivo local anesthetic activity of percutaneously injected site 1 sodium channel blockers", Anesthesiology, 90:524-34(1999).
Kushla, et al., "Noninvasive assessment of anesthetic activity of topical lidocaine formulations", J Pharm Sci, 82:1118-22 (1993).
Masters, et al., "Prolonged regional nerve blockade by controlled release of local anesthetic from a biodegradable polymer matrix" Anesthesiology, 79 (2):340-346 (1993).
Middleton, "Mechanism of action of surfactants on water binding properties of isolated stratum corneum", J Soc Cosmet Chem. ,20:399-403 (1969).
Padera, et al., "Tetrodotoxin for prolonged local anesthesia with minimal myotoxicity", Muscle Nerve, 34:747-53 (2006).
Ribaud, et al., "Organization of stratum corneum lipids in relation to permeability: influence of sodium lauryl sulfate and preheating", Pharm Res 11:1414-8 (1994).
Sagie and Kohane, "Prolonged sensory-selective neve blockade", Natl. Acad. Sci, 107(8):3740-5 (2010).
Sakura, et al., "Local anesthetic neurotoxicity does not result from blockade of voltage-gated sodium channels", Anesth Analg., 81:338-46 (1995).
Simons, et al., "Effect of chemical permeation enhancers on nerve blockade", Mol Pharmaceutics, 6:265-73 (2009).
Zanen, et al., "The optimal particle size for parasyrnpathicolytic aerosols in mild asthmatics", Int J Pharm., 114:111-5. (1995).

* cited by examiner

CHEMICAL PERMEATION ENHANCERS ENHANCE NERVE BLOCKADE BY TOXINS

CROSS REFERENCE TO RELATED APPLICATIONS

This application is a national phase filing under 35 U.S.C. 371 of PCT/US2009/044548 filed under the Patent Cooperation Treaty on May 19, 2009, which claims priority to and benefit of U.S. Provisional Patent Application No. 61/054,398, filed on May 19, 2008, entitled "Chemical Permeation Enhancers of Nerve Blockade" by Daniel S. Kohane and Emmanuel J. Simons, the contents of these applications are hereby incorporated by reference in their entirety.

GOVERNMENT SUPPORT

This invention was made with government support under Grant No. GM073626 awarded by National Institute of General Medical Sciences. The government has certain rights in the invention.

FIELD OF THE INVENTION

This relates generally to methods and compositions enhancing nerve blockade with local anesthetics.

BACKGROUND OF THE INVENTION

Local anesthetics must penetrate the epineurium, perineurium, and endoneurium in order to reach their intended sight of action. Consequently, local anesthetics require much higher concentrations to be effective when used clinically than in isolated nerves (Schwartz, et al., J Physiol, 233:167-194 (1973); Hahin, et al., J Gen Physiol, 78:113-139 (1981); Chernof, et al., *Biophys J.,* 58:69-81 (1990); Lee, et al., *Anesthesiology,* 77:324-335 (1992); Kohane, et al., *Anesthesiology,* 89:1199-1208 (1998)). The literature suggests that a small molecule's hydrophobicity has a U-shaped effect on its ability to penetrate biological barriers (Bernards and H. F. Hill, *Anesthesiology* 77(4):750-6 (1992)): drugs with an intermediate degree of hydrophobicity penetrate more effectively than those that are very hydrophobic or very hydrophilic. There are some data to suggest that this relationship holds true for local anesthetics penetrating to or into peripheral nerve (Barnet, et al., *Pain* 110:432-438 (2004)).

A number of methods have been used in the attempt to increase the duration of action of local anesthetics. A method currently used in medical practice is the co-administration of vasoconstrictors such as epinephrine (adrenaline), phenylephrine, or norepinephrine, which increase the residence time of the drug at the site of administration, due to the induction of vasoconstriction with subsequent reduction of systemic uptake of the local anesthetic or biodegradable polymer matrices (U.S. Pat. No. 5,618,563) and glucocorticoids (U.S. Pat. No. 5,700,485).

Chemical permeation enhancers (CPEs) have been used to increase the permeability of the lipid-protein barriers of the skin, and thereby increase drug flux, for over thirty years (Bauerova, K. et al., *Eur J Drug Metab Pharmacokinet* 200126(1-2): 85-94; Asbill, C. S., et al. *Crit Rev Ther Drug Carrier Syst* 17(6): 621-658 (2000); Kanikkannan, N., *Curr Med Chem* 7(6):593-608 (2000); Karande, et al., *J Control Release* 110:307-313 (2006)). Surfactants, a heterogeneous group of amphiphilic organic molecules with hydrophilic heads and hydrophobic tails, are a well-known class of CPEs. Several sub-classes of surfactants have been studied in the context of transdermal permeation, and are believed to reversibly modify lipids by adsorption at interfaces and removal of water-soluble agents that act as plasticizers (Middleton, J. D. *J Soc Cosmet Chem* 20:399-403 (1969); Ribaud, C., et al. *Pharm Res* 11:1414-1418 (1994)). Cationic surfactants are known to produce greater increases in permeant flux than anionic surfactants, which, in turn, increase permeability more than nonionic surfactants (Stoughton, R. B. In: E. M. Farber (Ed.), Psoriasis, Grune and Stratton, Orlando, Fla., 1982. p. 346-398; Kushla, et al., *J Pharm Sci* 82:1118-1122 (1993); Shen, et al., *J Pharm Sci* 65:1780-1783 (1976)). A broad range of non-surfactant chemical enhancers has also been investigated (e.g., alcohols, sulfoxides, polyols, fatty acids, esters, terpenes, and cyclodextrins), (Middleton, *J Soc Cosmet Chem* 20:399-403 (1969); Ribaud, C., et al. *Pharm Res* 11:1414-1418 (1994); Stoughton, R. B., In: E. M. Farber (Ed.), Psoriasis, Grune and Stratton, Orlando, Fla., 1982. p. 346-398; Kushla, G. P., *J Pharm Sci,* 82:1118-1122 (1993); Shen, W. W., et al., *J Pharm Sci* 65:1780-1783 (1976); R. B. Walker and E. W. Smith. *Adv Drug Delivery Rev,* 18:295-301 (1996)).

U.S. Pat. No. 6,455,066 to Fischer, et al., for example, describes the use of intradermal penetrating agents triglyceride, an aloe composition, and a mixture thereof for topical local anesthetic administration. U.S. Pat. No. 6,673,363 to Luo, et al. describes the use of organic or inorganic permeation enhancers for the delivery of anesthetic agents. U.S. Pat. No. 6,326,020 to Kohane, et al., describes the combination of naturally occurring site 1 sodium channel blockers such as tetrodotoxin with other agents such as another local anesthetic, a vasoconstrictor, glucocorticoid, adrenergic drugs, or amphiphilic or lipophilic solvent to improve the duration of block.

There is still a need for a composition that can provide prolonged nerve block while avoiding systemic toxicity.

It is an object of the present invention to provide a composition for use as an anesthetic with increased potency and efficacy.

It is still another method of the invention to provide a method for local anesthesia that avoids systemic toxicity due to the local anesthetic and provides prolonged nerve block.

SUMMARY OF THE INVENTION

Combinations of site I sodium channel blocker local anesthetics with chemical penetration enhancers have been developed to improve the potency and efficacy of local anesthetics, thereby decreasing their systemic toxicity without increasing local toxicity. The duration of block is greatly prolonged by combining the local anesthetic with a chemical penetration enhancer. In one embodiment, the local anesthetic is a hydrophilic local anesthetic. In a preferred embodiment, the local anesthetic is a Site I sodium channel blocker such as tetrodotoxin. Chemical permeation enhancers (CPEs) improve access of local anesthetics to the nerve, thereby improving their performance.

Surfactants, representing three CPE sub-groups: anionic, cationic, and nonionic surfactants, were co-injected with tetrodotoxin (TTX) or bupivacaine at the sciatic nerve of Sprague-Dawley rats. All enhancers produced marked concentration-dependent improvements in the frequency and duration of block with TTX but not bupivacaine. An in vitro toxicity assay showed a wide range of CPE myotoxicity, but in vivo histological assessment showed no signs of muscle or nerve damage at concentrations of CPEs that produced a half-maximal increase in the duration of block of TTX. There was no systematic relationship between the enhancers' charge or hydrophobicity and their enhancement of block duration or potency. Thus, CPEs can provide marked prolongation of nerve blockade from TTX, without apparent local tissue toxicity, and therefore enhance the clinical applicability of TTX for prolonged-duration local anesthesia.

DETAILED DESCRIPTION OF THE INVENTION

I. Definitions

Figure 1:
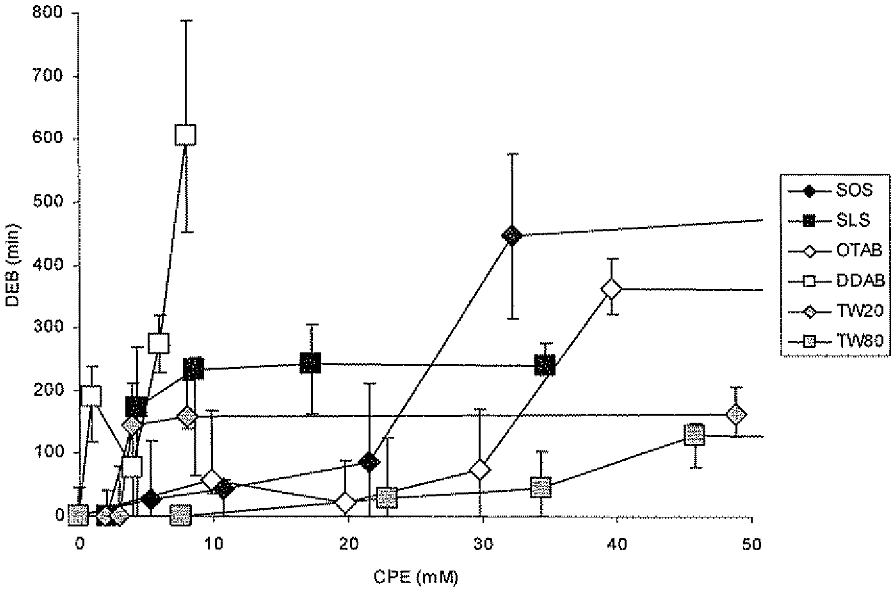
FIG. 1 is a graph showing the effect of different chemical penetration enhancers (SOS, SLS, OTAB, DDAB, TW 20, and TW 80) on the duration of sensory block from 30 μM TTX.

As used herein, chemical penetration enhancer (CPE) denotes any agent which can alter a biological barrier to enhance permeant flux or a chemical agent capable of reducing the surface tension of a liquid in which it is dissolved. The CPE is preferentially a surfactant, most preferably a cationic surfactant.

As used herein, local anesthetic (LA) refers to any agent that produces nerve blockage within a specific area, region or site.

"Aryl", as used herein, refers to -, 6- and 7-membered aromatic, heterocyclic, fused aromatic, fused heterocyclic, biaromatic, or bihetereocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amide, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, (uranyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has or fewer carbon atoms in its backbone (e.g., C1-C30 for straight chain, C3-C30 for branched chain), preferably 20 or fewer carbons, more preferably 10 or fewer carbons, most preferably 5 or fewer carbons. Likewise, preferred cycloalkyls have from 3-10 carbon atoms in their ring structure, and more preferably have 5, 6 or 7 carbons in the ring structure. The alkyl group can be substituted with one or more substituents including, but not limited to, alkyl, aryl, halogen, hydroxy, and thiol.

II. Compositions

The composition is designed to prolong the duration of a local anesthetic block, with no systemic toxicity. The composition consist of a local anesthetic in combination with one or more chemical penetration enhancers in amounts effective to prolong the duration of block of the local anesthetic, with no significant systemic toxicity, and is administered in a pharmaceutically acceptable carrier. The preferred composition contains a site 1 sodium channel blocker. The composition is administered in a formulation locally at the site where the nerve is to be blocked, preferably as a solution. The chemical penetration enhancer is preferably a charged penetration enhancer. In a preferred embodiment, the chemical penetration enhancer is a charged surfactant.

A. Site 1 Sodium Channel Blocker Local Anesthetics

Site I sodium channel blockers include tetrodotoxin (TTX), saxitoxin (STX), decarbamoyl saxitoxin, neosaxitoxin, and the gonyautoxins (referred to jointly herein as "toxins"). The preferred toxins are TTX and STX.

Tetrodotoxins are obtained from the ovaries and eggs of several species of puffer fish and certain species of California newts. Chemically, it is an amino perhydroquinaoline. See Kao, *Pharmacological Reviews,* 18(2):997-1049 (1966). Tetrodotoxin alone is too toxic to be used as an anesthetic.

Saxitoxin was first extracted from the Alaska butterclam, *Saxidomus gigantcus*, where it is present in algae of the genus *Gonyaulax*. The reported chemical formula is $C_{10}H_{15}N_7O_3$.2HCl. It is believed the toxin has a perhydropurine nucleus in which are incorporated two guanidinium moieties. Saxitoxin is too toxic to be used alone as a local anesthetic.

A number of unusual polypeptides have been isolated from the paralytic venoms of the fish hunting cone snails of the genus *Conus* found in the Philippine archipelago. Many of these, designated "conotoxins," have been discovered to affect ion channel function. The paralytic a, m, and w conotoxins block nicotinic acetylcholine receptors, sodium channels, and voltage sensitive calcium channels, respectively (reviewed in Olivera, et al., *Science,* 249:257-263 (1990)). Those which block sodium channels can be used in the same manner as the tetrodotoxins and saxitoxins.

B. Chemical Penetration Enhancers

Any biocompatible CPE can be administered in combination with the local anesthetic, either slightly before, after or with the local anesthetic.

Suitable penetration enhancers include sulfoxide decylmethylsulfoxide ($C_{10}$MSO); ethers such as diethylene glycol monoethyl ether, dekaoxyethylene-oleylether, and diethylene glycol monomethyl ethers; surfactants such as sodium lauryl sulfate (SLS), sodium octyl sulfate (SOS), dodecyltriethylammonium bromide (DDAB), octyltriethylammonium bromide (OTAB), TWEEN® 20 (polysorbate 20) and TWEEN® 80 (polysorbate 20), fatty acids such as C8-C22 and other fatty acids, C8-C22 fatty alcohols, and polyols.

Surfactants can be used in combination with other (non-surfactant) CPEs to enhance blockade.

The preferred CPEs are shown in Table 1:

TABLE 1

Properties of the chemical penetration enhancers (CPEs).

| CPE | MW | Length of Carbon Chain |
|---|---|---|
| Sodium Octyl Sulfate (SOS) | 232.28 | 8 |
| Sodium Dodecyl Sulfate (SLS) | 288.38 | 12 |
| Octyl-trimethyl-ammonium Bromide (OTAB) | 252.23 | 8 |
| Dodecyl-trimethyl-ammonium Bromide (DDAB) | 308.34 | 12 |
| Tween 20 (TW 20) | 1228 | 12 |
| Tween 80 (TW 80) | 1310 | 17 |

These have the following chemical structures.

| CPE/CLASS | Structure |
|---|---|
| SOS Anionic | 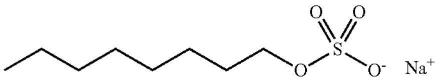 |
| SLS Anionic | 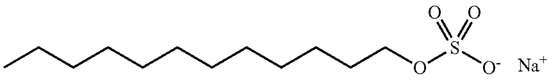 [SMILES: CCCCCCCCCCCCOS(=O)(=O)[O-] ; [Na+]] |
| OTAB Cationic | 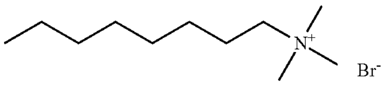 |
| DDAB Cationic | 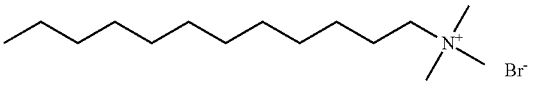 [SMILES: CCCCCCCCCCCC[N+](C)(C)C ; [Br-]] |
| TW 20 Nonionic | 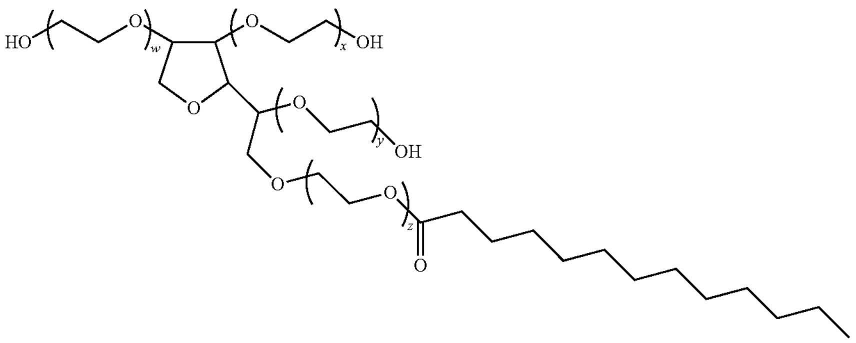 |

w + x + y + z = 20

-continued

| CPE/CLASS | Structure |
|---|---|
| TW 80 Nonionic | 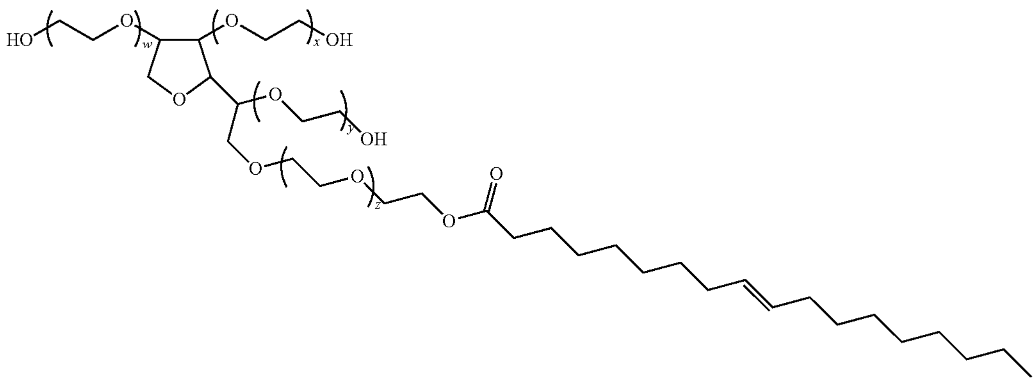 w + x + y + z = 20 |

Other suitable penetration enhancers include, but are not limited to, urea, (carbonyldiamide), imidurea, N,N-diethylformamide, N-methyl-2-pyrrolidine, 1-dodecal-azacyclopheptane-2-one, calcium thioglycate, 2-pyyrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as Brij® 76 (stearyl poly(10 oxyethylene ether), Brij® 78 (stearyl poly (20)oxyethylene ether), Brij® 96 (oleyl poly(10)oxyethylene ether), and Brij® 721 (stearyl poly(21)oxyethylene ether) (ICI Americas Inc. Corp.). Fatty acids such as linoleic acid, capric acid, lauric acid, and neodecanoic acid, which can be in a solvent such as ethanol or propylene glycol, can be used as lipid bilayer disrupting agents. Vegetable oils, such as peanut oil, may also be used as a penetration enhancer.

U.S. Pat. No. 4,537,776 to Cooper contains a summary of prior art and background information detailing the use of certain binary systems for permeant enhancement. European Patent Application 43,738, also describes the use of selected diols as solvents along with a broad category of cell-envelope disordering compounds for delivery of lipophilic pharmacologically-active compounds. A binary system for enhancing metaclopramide penetration is disclosed in UK Patent Application GB 2,153,223 A, consisting of a monovalent alcohol ester of a C8-32 aliphatic monocarboxylic acid (unsaturated and/or branched if C18-32) or a C6-24 aliphatic monoalcohol (unsaturated and/or branched if C14-24) and an N-cyclic compound such as 2-pyrrolidone or N-methylpyrrolidone.

Combinations of enhancers consisting of diethylene glycol monoethyl or monomethyl ether with propylene glycol monolaurate and methyl laurate are disclosed in U.S. Pat. No. 4,973,468 for enhancing the transdermal delivery of steroids such as progestogens and estrogens. A dual enhancer consisting of glycerol monolaurate and ethanol for the transdermal delivery of drugs is described in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 discloses penetration-enhancing compositions for topical application including an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Liposomes are microscopic aggregates if highly ordered lipid molecules which are normally dispersed in a hydrophilic solvent. Liposomes have been shown to enhance the permeability of drugs (reviewed in Choi, et al., *J. Pharmacol and Biophys. Res.,* 18(5):209-19 (2005). In another embodiment, suspensions in chromophores conventionally used in the art to enhance permeation are used. The local anesthetic can also be administered as an emulsion, such as an oil-in-water or a water-in-oil emulsion.

C. Combinations of Anesthetic and Active Agents and/or CPE

The local anesthetic and CPE can be combined into a single dosage form or sequentially administered. The effective amount and ratio of CPE to anesthetic is dependent on the anesthetic, the CPE, the site of administration, and the species into which the anesthetic is administered. More specifically, dosage and concentrations will change depending on the size of nerve, species, anatomic location (peripheral nerve, epidural space, intrathecal), and even the volume of injectate. The concentration and dosages can be determined as demonstrated in the examples.

In general, the concentrations will be within the following ranges, although the range may be greater.

Site 1 Sodium Channel Blockers:

For TTX: 10-120 micromolar.

For saxitoxin: 5-60 micromolar

For neosaxitoxin: 3-40 micromolar

For decarbamoyl STX 30-480 micromolar

These numbers are derived from: Kohane D S, Lu N T, Gokgol-Kline A C, Shubina M, Kuang Y, Hall S, Strichartz G R, Berde C B, "The local anesthetic properties and toxicity of saxitonin homologues for rat sciatic nerve block in viva", *Reg Anesth Pain Med* 25: 52-9 (2000).

In applications where the volume delivered is very small, the concentrations could be up to 100 times higher.

CPE Range of Concentrations:

SOS: 10-100 mM

SLS: 1-40 mM

DDAB: 0.5-10 mM

OTAB: 20-120 mM

Tween® 20: 3-50 mM

Tween® 80: 20-80 mM

These numbers are derived from: Simons E J, Bellas E, Lawlor M W, Kohane D S: Effect of chemical permeation enhancers on nerve blockade. Mol Pharmaceutics 2009; 6: 265-273.

In another embodiment, these agents are co-injected with a vasoconstrictor.

In still another embodiment, the site I sodium channel blocker is combined with another local anesthetic. Useful local anesthetics include amino-amide or amino-ester local anesthetics, any at least partly amphiphilic local anesthetics, local anesthetics that act not on the surface of the cell, and any at least partly charged local anesthetics.

In one embodiment, the local anesthetic is a charged local anesthetic, preferably a permanently charged local anesthetic. Preferred charged local anesthetics are those of Formula I or Formula II:

Formula I

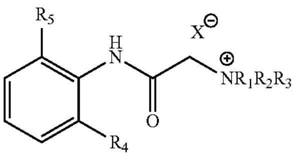

Formula II

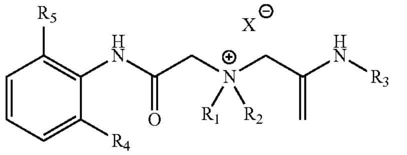

where $R_1$-$R_5$ are independently selected from hydrogen; linear, branched, or cyclic alkyl and aryl groups.

Suitable local charged anesthetics of Formula I and II include, but are not limited to, charged lidocaine derivatives, such as QX-314 ((N-(2,6)dimethylphenylcarbamoylmethyl triethylammonium bromide); QX-222 (2-((2,6-dimethylphenyl)amino)-N,N,N-trimethyl-2-oxoethanaminium); QX-572 (N,N-bis(phenylcarbamoylmethyl)-dimethylammonium chloride).

QX-314 is a quaternary lidocaine derivative that is permanently charged and lipophobic. QX-314 is a powerful blocker of voltage-sensitive Na+ conductance when applied intracellularly. QX-314 suppresses the generation of Na+-dependent spikes from inside the cell membrane, without affecting Ca2+ currents or glutamate-activated currents. Other suitable charged anesthetics include, but are not limited to, tonicaine.

The structures of QX-314, QX-222, QX-572, and tonicaine are shown below:

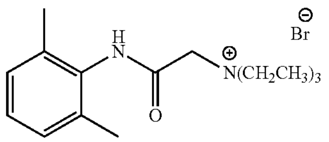

QX-314

-continued

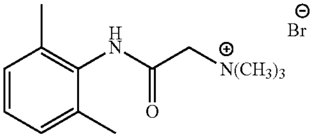

QX-222

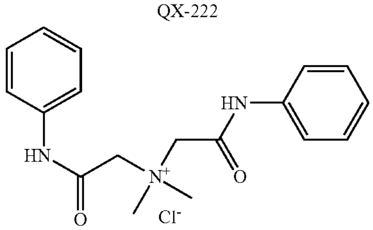

QX-572

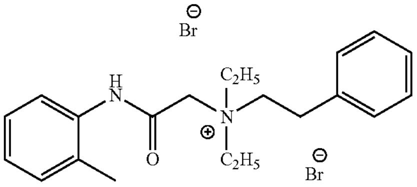

Tonicaine

Other suitable charged local anesthetics include, but are not limited to, charged tetracaine derivatives (e.g., N-butyl tetracaine) and permanently charged derivatives of flecainide.

In one embodiment, the local anesthetic is in an excipient having a pH that causes the local anesthetic to be charged.

D. Formulations

The compounds described herein can be formulated for parenteral or topical formulation. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

Parenteral Formulations

The compounds described herein can be formulated for parenteral administration. "Parenteral administration", as used herein, means administration by injection.

The preparation of an aqueous composition that contains one or more of the compounds described herein is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, and emulsomes (see U.S. Pat. No. 5,716,637 to Anselem et al.).

The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In many cases, it will be preferable to include isotonic agents, for example, sugars or sodium chloride.

Solutions of the active compounds as the free acid or base or pharmacologically acceptable salts thereof can be prepared in water suitably mixed with one or more pharmaceutically acceptable excipients including, but not limited to, surfactants, dispersants, emulsifiers, pH modifying agents, and combination thereof. Dispersions also can be prepared in glycerol, liquid polyethylene glycols, and mixtures thereof and in oils, such as vegetable oils, e.g., peanut oil, corn oil, sesame oil, etc. Dispersions can contain one or more of the pharmaceutically acceptable excipients listed above.

Suitable surfactants to facilitate formulation may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Pluronic® L121 (Poloxamer 401), stearoyl monoisopropanolamide, and polyoxyethylene hydrogenated tallow amide. Examples of amphoteric surfactants include sodium N-dodecyl.beta.-alanine, sodium N-lauryl.beta.-iminodipropionate, myristoamphoacetate, lauryl betaine and lauryl sulfobetaine.

Under ordinary conditions of storage and use, the formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Controlled Release Formulations

The parenteral formulations described herein can be formulated for controlled release including immediate release, delayed release, extended release, pulsatile release, and combinations thereof. The compositions can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the body by means including enzymatic degradation and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to, hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila., Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten. Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Injectable/Implantable Solid Implants

The compositions described herein can be incorporated into injectable/implantable solid implants, such as polymeric implants. In one embodiment, the compositions are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compositions can be incorporated into a polymer matrix and molded or compressed into a device that is a solid at room temperature. For example, the compositions can be incorporated into a biodegradable polymer, such as polyanhydrides and copolymers thereof, polyhydroalkanoic acids and copolymers thereof, PLA, PGA, and PLGA, and compressed into solid device, such as disks, or extruded into a device, such as rods.

Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

The term aerosol as used herein refers to any preparation of a fine mist of particles, which can be in solution or a suspension, whether or not it is produced using a propellant. Aerosols can be produced using standard techniques, such as ultrasonication or high pressure treatment. See, for example, Adjei, A. and Garren, J. Pharm. Res., 7: 565-569 (1990); and Zanen, P. and Lamm, J.-W. J. Int. J. Pharm., 114: 111-115 (1995). Preferably, the aqueous solutions is water, physiologically acceptable aqueous solutions containing salts and/or buffers, such as phosphate buffered saline (PBS), or any other aqueous solution acceptable for administration to a animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the compositions. An appropriate solvent should be used that dissolves the compositions or forms a suspension of the compositions. The solvent should be sufficiently volatile to enable formation of an aerosol of the solution or suspension. Additional solvents or aerosolizing agents, such as freons, can be added as desired to increase the volatility of the solution or suspension.

III. Methods of Administration

The composition can be used for any of the methods for administering local anesthetics known to one of ordinary skill in the art. The composition can be formulated for topical anesthesia, infiltration anesthesia, filed block anesthesia, nerve block anesthesia, intravenous regional anesthesia, spinal anesthesia and epidural anesthesia.

The anesthetic will typically be provided as a solution or as a lyophilized powder or in crystalline form which is reconstituted at the time of use with a diluent typically packaged with the anesthetic. Either may include the CPE. For a site I sodium channel blocker such as TTX/STX, the CPE will be present in excess due to the extremely small amount of local anesthetic required. The anesthetic will typically be relatively dilute for safety reasons, as described in the examples. The solution is typically slightly acidic for stability reasons, but would depend on the CPE. The pH is important to the extent that most site 1 blockers are stored (if a liquid) in acidic pH (typically less than 5.5).

IV. Examples

The present invention will be further understood by reference to the following non-limiting examples.

Example 1

Comparison of Site I Sodium Channel Blocker or Local Anesthetic with and without Surfactant CPE Materials and Methods Animal Care.

Young adult male Sprague-Dawley rats (350-420 g) were obtained from Charles River Laboratories (Wilmington, Mass.) and housed in groups of two per cage on a 6 a.m. to 6 p.m. light/dark cycle. All animals were cared for in accordance with protocols approved institutionally and nationally.

Chemical Enhancers & Solution Preparation.

Representative enhancers from three different classes of surfactants were obtained from Sigma (St. Louis, Mo.): sodium lauryl sulfate (SLS) and sodium octyl sulfate (SOS), anionic surfactants; dodecyltriethylammonium bromide (DDAB) and octyltriethylammonium bromide (OTAB), cationic surfactants; and Tween® 20 (polysorbate 20) and Tween® 80 (polysorbate 80), nonionic surfactants (Table 1).

Tetrodotoxin (TTX) and bupivacaine (Sigma) solutions were prepared in saline individually and in combination with each enhancer the night before scheduled injections. TTX and bupivacaine concentrations were chosen to be near the bottom of their respective dose-response curves (Kohane, et al., *Anesthesiology,* 89:1199-1208 (1998); Kohane, et al., *Reg Anesth Pain Med,* 26:239-45 (2001); enhancer concentrations were initially chosen to be approximately 50% of those used successfully in transdermal applications, followed by lower and higher concentrations as needed to obtain a dose-response curve.

Sciatic Blockade Technique.

Animals were cared for in compliance with protocols approved by the Massachusetts Institute of Technology (MIT) Committee on Animal Care, in conformity with the NIH guidelines for the care and use of laboratory animals (NIH publication #85-23, revised 1985). Rats were anesthetized using isoflurane in oxygen. A 23-guage needle was introduced posteromedial to the greater trochanter, and 0.3 mL of the drug+/−enhancer solution was injected upon contacting bone. To generate the dose-response curves for the CPEs, four animals were injected with each CPE at 5 different concentrations (each alone and with 30 μM TTX). Larger sample sizes were obtained at the following concentrations that were important for further experiments: 11 mM SOS, 2 mM SLS, 9 mM SLS, 17 mM SLS, 35 mM SLS, 46 mM Tween 80 (n=8); 4 mM SLS (n=16); and 23 mM Tween 80 (n=22). For CPEs injected with 1.39 mM bupivacaine, n=4 for each CPE-bupivacaine combination. A total of 12 animals were injected with 1.39 mM bupivacaine alone (no CPE).

Assessment of Nerve Blockade.

In all experiments, the experimenter was blinded as to what treatment any given rat had received. Presence and extent of nerve blockade was investigated as previously described (Kohane, et al., *Anesthesiology,* 89:1199-1208 (1998); Padera, et al., *Muscle Nerve,* 34:747-53 (2006); Kohane, et al., *Anesthesiology,* 89:119-31 (1998); Masters, et al., *Anesthesiology,* 79(2):340-346 (1993)). Erratum in: *Anesthesiology,* 79(5): 1160 (1993)). Briefly, thermal nociception of each leg was assessed, with the right (uninjected) leg serving as an untreated control.

Thermal nociception was assessed by a modified hotplate test. Hind paws were exposed in sequence (left then right) to a 56° C. hot plate (Model 39D Hot Plate Analgesia Meter, IITC Inc., Woodland Hills, Calif.). The time (latency) until paw withdrawal was measured with a stopwatch. If the animal did not remove its paw from the hot plate within 12 seconds, it was removed by the experimenter to avoid injury to the animal or the development of hyperalgesia. The duration of thermal nociceptive block was calculated as the time required for thermal latency to return to a value of 7 seconds from a higher value. Seven seconds is the midpoint between a baseline thermal latency of approximately 2 seconds in adult rats, and a maximal latency of 12 seconds. Latencies>7 sec were considered to be effective blocks.

Kohane, et al., *Anesthesiology,* 89:1199-1208 (1998); Kohane, et al., *Anesthesiology,* 90:524-34 (1999 demonstrated >99% successful blocks with 0.1-0.3 mL of 0.25%-0.5% (8.7-17 mM) bupivacaine, indicating that differences in block duration reflected actual pharmacological differences rather than operator error.

Tissue Harvesting and Histology.

Animals were euthanized with carbon dioxide, and the sciatic nerves and adjacent tissues were harvested for histology. Tissues were fixed in Accustain (formalin-free fixative) company, city, state, embedded in paraffin, sectioned, and stained with hematoxylin and eosin by the Department of Comparative Medicine at MIT (fee for service), using standard techniques.

Cell Culture.

C2C12, a mouse myoblast cell line (American Type Culture Collection, ATCC, CRL-1772, Manassas, Va.) was cultured to proliferate in Dulbecco's Modified Eagle's Medium (DMEM) supplemented with 20% Fetal Bovine Serum and 1% Penicillin Streptomycin (Pen Strep). All cell culture supplies were purchased from Invitrogen (Carlsbad, Calif.) unless otherwise noted. Cells were plated in 24-well tissue culture plates with 50,000 cells/mL/well in DMEM supplemented with 2% Horse Serum and 1% Pen Strep, and left to differentiate into myotubules for 10-14 days. During differentiation, media was exchanged every 2 to 3 days. After one week of myotube differentiation, 100 μL of the 10× enhancer+/−TTX containing media was added to 900 μL of fresh media; 100 μL of PBS was added in control wells. The enhancer solution was prepared by dissolving the enhancer in PBS and stirring overnight. The solution was filtered aseptically using a 0.2 μm syringe filter. The TTX, or PBS for groups not containing drug, was added aseptically to the enhancer solution. At 2, 8, 24, or 96 hours the plates were assayed as described below. Cells were maintained at 37° C. in 5% $CO_2$ balance air.

Assessing Viability.

Cell viability was assessed using a colorimetric assay (MTT kit, Promega G4100 Madison, Wis.) in which a yellow tetrazolium salt (MTT) is metabolized in live cells to form insoluble purple formazan crystals. The purple crystals are solubilized by the addition of a detergent, and the color is then be quantified spectrophotometrically. At each time point 150 μL of MTT reagent was added to the cells. Following a four hour incubation at 37° C., 1 mL of solubilization solution (detergent) was added. The absorbance was read at 570 nm using the SpectraMax 384 Plus fluorometer (Molecular Devices, Sunnyvale, Calif.) after overnight incubation. Cells were also monitored visually to confirm the results of the MTT assay. Each plate contained media only wells whose absorbance was subtracted from the rest of the plate as noise. All groups were then normalized to blank media.

Statistical Analysis.

In vivo neurobehavioral data were not normally distributed, and are therefore presented as medians with $25^{th}$ and $75^{th}$ percentiles and compared by Mann-Whitney U-test. MTT assay results are described parametrically with means+/−standard deviations and compared by t-tests and analysis of variance (ANOVA). Statistical significance, for both parametric and nonparametric tests, was defined as $P<0.05$.

Results

Effect of Enhancers on Nerve Blockade with TTX

Injection of 0.3 mL of 30 μM TTX caused sensory blockade in 29% of animals tested (n=24). The median duration of block was 0 minutes, with $25^{th}$ and $75^{th}$ percentiles of 0 minutes and 47 minutes, respectively. The selected concentration was based on Kohane, et al., *Anesthesiology,* 89:119-31 (1998) and chosen for further studies as improvement of nerve blockade could easily be detected. Dose-response curves were obtained for the duration of block from 30 μM TTX with varying concentrations of SLS and SOS (anionic surfactants), DDAB and OTAB (cationic surfactants), and Tween® 20 and Tween® 80 (nonionic surfactants) individually (FIG. 1). The group that received DDAB was also injected with 30 μM TTX in 32 mM of the enhancer, but none of those rats' nerve blocks resolved (returned to normal).

In most cases, the enhancers demonstrated a concentration-dependent increase in block duration before reaching a plateau. This maximal duration of block was used as a measure of efficacy for all CPEs except for DDAB, where the longest duration of block from which the animals recovered was used. There was a range of maximum durations of block due to the CPEs, the greatest being seen with DDAB (median maximum duration of block=606 minutes; FIG. 1, Table 2).

TABLE 2

Effect of chemical penetration enhancers (CPEs) on the duration of nerve blockade from TTX.

| TTX 30 μM with: | Maximum Block Duration (MBD, minutes) | $EC_{MBD}$ (mM) | $EC_{100\,min}$ (mM) | $EC_{50eff}$ (mM) |
|---|---|---|---|---|
| — | 0 (0-47) | — | — | — |
| SOS | 521 (361-669) | 86 | 22 | 32 |
| SLS | 240 (255-277) | 35 | 3 | 4 |
| OTAB | 353 (327-361) | 119 | 31 | 30 |
| DDAB | 606 (452-788) | 8 | 1 | 6 |
| TW 20 | 163 (129-206) | 49 | 4 | 3 |
| TW 80 | 120 (111-143) | 81 | 40 | 34 |

CPEs markedly prolonged the maximum block duration (MBD) from 30 μm TTX. The $EC_{MBD}$ is the CPE concentration that caused the maximum prolongation of block from 30 μm TTX. The $EC_{100min}$ is the interpolated concentration of CPE that increased the block duration of 30 μm TTX to 100 min. The $EC_{50eff}$ is the concentration of a given CPE that caused a half-maximal increase in duration of block (half-MBD) of 30 μm TTX. Block durations are medians with $25^{th}$ and $75^{th}$ percentiles in parentheses; n=4 for all CPE concentrations, except those specified in Materials and Methods (where n=8-22).

As shown in Table 3 below, all the CPEs increased the percentage of animals that developed effective nerve block from 29.2% with TTX alone to 88-100%.

TABLE 3

Concentrations of chemical penetration enhancers (CPEs) producing maximal frequency of nerve blockade with 30 μM TTX.

| TTX 30 μm with: | Highest % Animals with Effective Block | CPE Concentration (mM) |
|---|---|---|
| — | 29 | — |
| SOS | 100 | 32 |
| SLS | 88 | 17 |
| OTAB | 100 | 40 |
| DDAB | 100 | 6 |
| Tween 20 | 100 | 4 |
| Tween 80 | 100 | 81 |

CPEs increased the percentage of animals developing effective block from 30 μm TTX. Blocks were considered effective if latency was >7 seconds at any point. The CPE concentration listed was the lowest needed to achieve the highest percentage of animals with block; n=4 for all conditions except TTX alone (n=24) and TTX+SLS (n=8).

At the concentrations needed to cause this maximum percentage of block, all CPEs significantly improved TTX block duration (for SOS, SLS, OTAB, DDAB, Tween® 20, and Tween® 80, $p<0.001$ compared to the duration of block from TTX alone). In general, the maximum prolongation of TTX block by the cationic surfactants (OTAB, DDAB) was statistically significantly greater than prolongation by the other CPEs. The maximum prolongation of TTX block by the nonionic surfactants (Tween® 20, Tween® 80) was generally less than that by the others ($p<0.05$ by Mann-Whitney U-test).

As a measure of the potency of the block-prolonging effect of the CPEs, it was determined by interpolation that the concentration of each enhancer required to achieve a duration of block of 100 minutes (the $EC_{100min}$, Table 2). Tween® 20, SLS, and DDAB were more potent (lower $EC_{100min}$) than Tween® 80, SOS, and OTAB (FIG. 1; Table 2). Within the classes of enhancers where the members differed only in the length of the carbon chain (SOS-SLS; OTAB-DDAB), those with the eight-carbon chain were less potent than those with the twelve-carbon chain. (In the case of the Tween® compounds, that relationship was reversed, but there are other significant differences in the Tween® structures.) Each enhancer was also injected alone, without TTX, to confirm that the increased duration of block was not due to analgesic or toxic effects of the enhancers themselves; with one exception (32 mM DDAB), the CPE alone did not cause nerve blockade.

Effect of Enhancers on Nerve Blockade with Bupivacaine.

1.39 mM (0.04%) bupivacaine had performance characteristics comparable to 30 μm TTX with respect to percentage of animals blocked and median duration of block (Table 4) by producing a dose-response curve of sciatic nerve blocks with six bupivacaine concentrations spanning the range 0.69 mM-6.9 mM, (n=4-12 rats per concentration). 1.39 mM bupivacaine was tested with each of the CPEs at a concentration that created a half-maximal increase in the duration of block of TTX, the $EC_{50eff}$ (Table 2). None of the 6 enhancers tested in these experiments resulted in a statistically significant change in the duration of bupivacaine nerve block as shown in Table 4.

TABLE 4

Effect of chemical penetration enhancers (CPEs) on frequency of nerve blockade from bupivacaine.

| Bupivacaine 1.4 mM with the $EC_{50eff\ of}$: | Duration of Sensory Block (minutes) | % Animals with Effective Block |
|---|---|---|
| — | 0 (0-34) | 42 (5/12) |
| SOS | 0 (0-8) | 25 (1/4) |
| SLS | 22 (0-60) | 50 (2/4) |
| OTAB | 0 (0-0) | 0 (0/4) |
| DDAB | 0 (0-0) | 0 (0/4) |
| Tween 20 | 0 (0-19) | 25 (1/4) |
| Tween 80 | 0 (0-0) | 0 (0/4) |

Duration and frequency of nerve block from bupivacaine with and without each of the CPEs at the $EC_{50eff}$ from Table 2a. Durations of effective block (DEB) are expressed as medians with $25^{th}$ and $75^{th}$ percentiles in parentheses. For bupivacaine alone, n=12; for bupivacaine+CPE, n=4.

In Vitro Toxicity.

Figure 2:
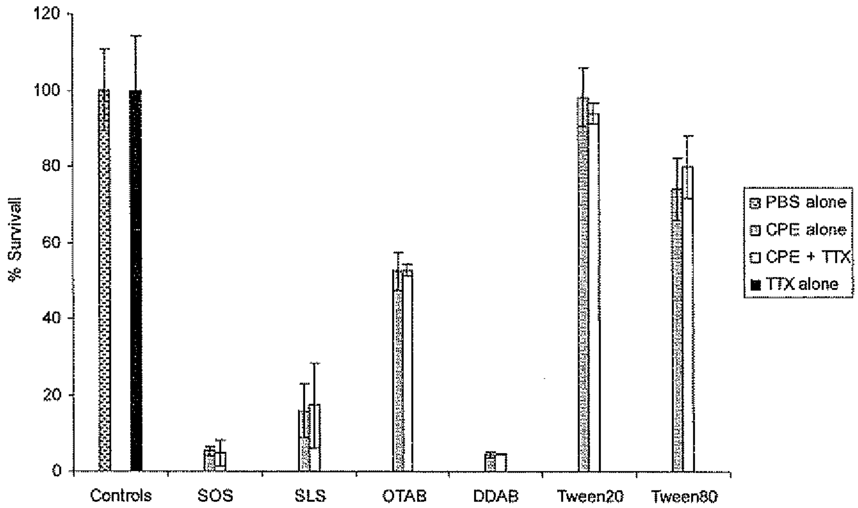
FIG. 2 is shows the survival of C2C12 myotubes after a 2-hour exposure to PBS or TTX alone (control) or to the $EC_{50eff}$ (CPE concentration that caused a half-maximal increase in block duration) of each CPE (SOS, SLS, OTAB, DDAB, Tween® 20 and Tween® 80) alone and with 30 μM TTX. Data are shown as means±standard deviations (n=4).

C2C12 myotube cultures were exposed to each enhancer at its $EC_{50eff}$ with and without TTX and assayed for viability after 2 hours (FIG. 2). The most toxic enhancers were DDAB and SOS, followed by SLS, OTAB, Tween®80, and Tween® 20, in order of decreasing toxicity. C2C12 viability decreased with increased duration of exposure to all CPEs except Tween®20, which remained at untreated-control levels after an 8-hour exposure (data not shown). Addition of TTX to the cell culture medium did not impact cell survival when given alone or in the presence of enhancers.

In Vivo Toxicity.

The sciatic nerves and surrounding muscle of rats injected with the $EC_{50eff}$ of each enhancer (i.e., the same concentration used in vitro), with and without TTX, were examined for evidence of inflammation and tissue injury four days after injection. Four animals were injected in each group.

Animals injected with the $EC_{50eff}$ SOS, SLS, OTAB, Tween® 20 and Tween® 80 showed no significant muscle or nerve injury, although some samples in all groups showed mild inflammation with macrophages and lymphocytes around the muscle and nerve, without evidence of infiltration, fibrosis, or atrophy within the muscle or nerve. Because Tween® 20 at its $EC_{50eff}$ showed no evidence of toxicity in vitro or in vivo, additional concentrations were tested to determine the highest sub-toxic concentration. Tween® 20 at 24.4 and 81.4 mM showed progressively worsening (mild to moderate) muscle atrophy and inflammation, similar in type but not severity to that seen with the DDAB $EC_{50eff}$. Note that 81.4 mM is more than twenty times the $EC_{50eff}$ of Tween® 20. Samples from animals injected with DDAB consistently showed moderate to severe infiltration of macrophages and lymphocytes, atrophy and degeneration of muscle fibers, and fibrosis of the tissue. An additional two animals were injected with 3% (97.3 mM) DDAB (the concentration at which animals developed irreversible nerve block). These showed deep and severe tissue damage, including ischemic necrosis, accompanied by severe and extensive inflammation.

Animals injected with the $EC_{50eff}$ of the enhancers together with 30 μm TTX showed the same histological results as those without TTX. Again, some of the samples exposed to DDAB showed severe lymphocytic inflammatory infiltration of muscle with degenerative changes, regenerative changes, and fibrosis. These samples also showed a mild lymphocytic infiltrate of nerve and focal fat necrosis.

Indicators of nerve fiber injury, including fibrosis and myelin ovoids, were not seen in any samples, but subtle degrees of damage to myelinated nerve fibers cannot be accurately assessed using paraffin-embedded, hematoxylin-eosin-stained sections.

Discussion

Surfactant CPEs caused a concentration-dependent increase in TTX-induced nerve block, but, at the concentrations tested here, did not enhance block from bupivacaine. This difference is due to TTX being extremely hydrophilic, having an obligate charge, while bupivacaine, like all amino-ester and amino-amide local anesthetics, can be conditionally hydrophobic due to its aromatic moiety and tertiary amine. There is a pH-dependent equilibrium between the cationic protonated form of bupivacaine that is water soluble and the neutral form that is soluble in organic solvents (i.e. is hydrophobic), and therefore partitions relatively easily into cell membranes and other biological barriers. The relatively pronounced improvement in block from TTX with CPEs relates to its lack of hydrophobicity, whereas bupivacaine does not benefit because its structure already permits easy crossing of biological barriers. High (millimolar) concentrations of adrenergic antagonists, far in excess of the range in which they are active on adrenergic receptors, greatly prolong the duration of block by TTX (Kohane, et al., *Reg Anesth Pain Med,* 26:239-45 (2001)). The results presented here support the view that the prolongation of nerve block by those polycyclic compounds was due to flux enhancement (i.e. those compounds were acting as CPEs).

Figure 3:
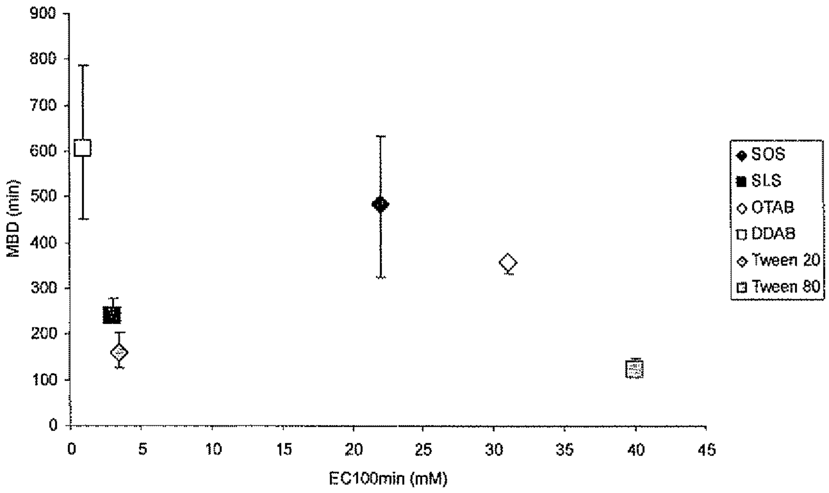
FIG. 3 is a graph showing the maximum block duration (MBD) plotted against interpolated $EC_{100min}$ values for each CPE. Anionic, cationic and nonionic surfactants are grouped by color (black, grey, and white respectively). Block durations are expressed as medians with $25^{th}$ and $75^{th}$ percentiles (n=4).

All the CPEs examined resulted in prolongation of TTX block. Though there was a considerable range in the magnitude of enhancement, no individual CPE or class of CPE (anionic, cationic, or nonionic surfactant) clearly performed better than all the others. The nonionic agents' block prolongations, though significant, were shorter than those of the other CPEs. This is consistent with the effects of surfactants on permeant flux across the stratum corneum and epidermis of the skin (Kushla, et al., *J Pharm Sci,* 82:1118-1122 (1993). The various CPEs resulted in a variety of patterns of block prolongation with respect to the magnitude of the increase in the maximum duration of block, or the improvement (reduction) in the $EC_{100min}$. It is important to be careful in using the $EC_{100min}$ to make comparative statements regarding potency, since the shapes of the dose-response curves for each CPE are not always similar. In general, the magnitude of the maximal improvement in duration of block (the maximum block duration, MBD) did not correlate well with the potency ($EC_{100min}$, FIG. 3). There also was no consistent pattern in the effect of hydrophobic chain length on duration of block.

Figure 4:
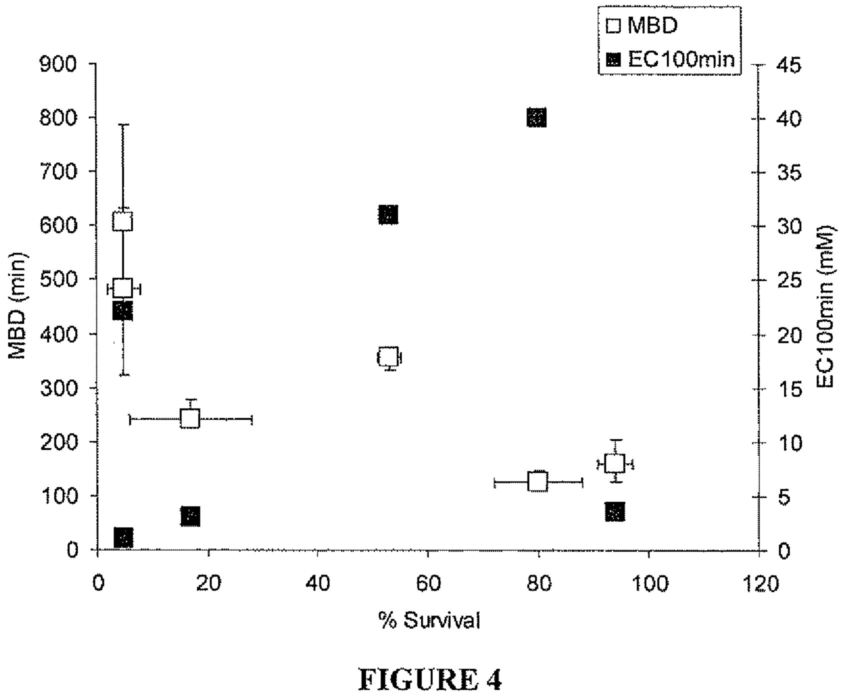
FIG. 4 shows MBD and $EC_{100min}$ plotted against cell survival. Cell survival data are means with standard deviations from C2C12 cells exposed to each CPE at its $EC_{50eff}$ for two hours. Block durations are expressed as medians with $25^{th}$ and $75^{th}$ percentiles.

CPEs varied widely in the cytoxicity of their $EC_{50eff}$. In general, the agents that produced the longest maximal block durations were more toxic in cell culture (FIG. 4, $R^2$=0.66). There was no correlation between the $EC_{100min}$ and toxicity ($R^2$=0.11). With the cationic surfactants, toxicity increased with molecular weight and carbon-chain length, while it decreased with the same parameters in anionic surfactants.

In assessing the balance between maximum block duration and cytotoxicity (shown in Table 5 below), Tween® 20 would appear to have the most favorable relevant ratios.

TABLE 5

Relationship between maximum block duration (MBD) and $EC_{100\,min}$, and in vitro viability.

| TTX 30 μm with: | % Survival | MBD / (100 − % Survival) | % Survival / $EC_{100\,min}$ |
|---|---|---|---|
| SOS | 5 ± 3 | 5.5 | 0.2 |
| SLS | 17 ± 11 | 2.9 | 5.7 |
| OTAB | 53 ± 2 | 7.5 | 1.7 |
| DDAB | 5 ± 0.2 | 6.4 | 5.0 |
| Tween 20 | 94 ± 3 | 27 | 24 |
| Tween 80 | 80 ± 8 | 6.0 | 2.0 |

The maximum block duration (Table 2), $EC_{100min}$ (Table 1), and in vitro survival data (determined from C2C12 MTT assay). The values for maximal block duration and $EC_{100\,min}$ are from Table 2; those for cell survival are derived from FIG. 2. Cell survival data are mean percentages with standard deviations. For the two ratios in the columns on the right, a high value is favorable (good ratio of performance to toxicity).

The in vivo data showed that all compounds, with the notable exception of DDAB, caused little or no tissue injury when delivered at the same concentrations as used in vitro (the $EC_{50eff}$, which had caused approximately half-maximal increase in duration of block from TTX). This discrepancy may be explained by differences between cultured cell lines and in vivo tissue, but it is also possible that the local concentration of the CPEs dissipates rapidly after injection in vivo. Tetrodotoxin itself caused little or no toxicity, with or without enhancers, a finding consistent with Kohane, et al., *Anesthesiology,* 89:1199-1208 (1998). The in vivo results indicate that enhancer toxicity can be minimal or non-existent within a concentration range that results in significant block duration, and that the most efficacious compounds could be used rather than those with the best toxicity profile from in vitro studies. There was little or no evidence of direct nerve injury in all the CPEs investigated, including concentrations of DDAB that resulted in long-term loss of nerve function.

Myotoxicity and neurotoxicity are well-known concomitants of conventional amino-ester and amino-amide local anesthetics, but not of tetrodotoxin (Padera, et al., *Muscle Nerve,* 34:747-53 (2006); Benoit, et al., *Toxicol. Appl. Pharmacol.,* 52:187-198 (1980); Sakura, et al., *Anesth Analg.,* 81:338-346 (1995). TTX's principal disadvantage is systemic toxicity, which is dose-limiting. In these experiements, CPEs dramatically increased the median duration of block from a very low concentration of TTX (e.g. from 0 to 353 min by use of OTAB). These durations of block far exceed those that could be achieved even by toxic, near-lethal concentrations of TTX in the absence of vasoconstrictors. For example, 50 μm TTX applied in the same manner without CPEs resulted in an average duration of block of approximately 150 minutes, but with a 20% mortality rate (Kohane, et al., *Anesthesiology,* 89:119-31 (1998). It follows that the use of CPEs would result in a marked improvement in the therapeutic index of TTX (the ratio of the effective to the lethal dose).

Flux enhancing agents caused a marked increase in nerve blockade duration from hydrophilic TTX, but did not improve block duration from amphiphilic bupivacaine. The prolongation of TTX block was provided by different types of surfactants. Although there was considerable cytotoxicity from some CPEs in vitro, histology from in vivo experiments showed little or no damage in muscle and nerve, except with DDAB.

Example 2

Effect Combining Site I Sodium Channel Blocker with Local Anesthetic

Materials and Methods

Animal Care

Young adult male Sprague-Dawley rats (350-420 g) were obtained from Charles River Laboratories (Wilmington, Mass.) and housed in groups of two per cage on a 6 a.m. to 6 p.m. light/dark cycle. All animals were cared for in accordance with protocols approved institutionally and nationally.

Chemical Enhancers & Solution Preparation

QX-314 and QX-222 (Sigma) solutions were prepared in saline individually the night before scheduled injections.

Sciatic Blockade Technique

Animals were cared for in compliance with protocols approved by the Massachusetts Institute of Technology (MIT) Committee on Animal Care, in conformity with the NIH guidelines for the care and use of laboratory animals (NIH publication #85-23, revised 1985). Rats were anesthetized using isoflurane in oxygen. A 25-guage needle was introduced posteromedial to the greater trochanter, and 300 μL injected upon contacting bone.

Assessment of Nerve Blockade

In all experiments, the experimenter was blinded as to what treatment any given rat had received. Presence and extent of nerve blockade was investigated as previously described (Kohane, et al., *Anesthesiology,* 89:1199-1208 (1998); Padera, et al., *Muscle Nerve,* 34:747-53 (2006); Kohane, et al., *Anesthesiology,* 89:119-31 (1998); Masters, et al., *Anesthesiology,* 79(2):340-346 (1993)). Briefly, thermal nociception of each leg was assessed, with the right (uninjected) leg serving as an untreated control.

Thermal nociception was assessed by a modified hotplate test. Hind paws were exposed in sequence (left then right) to a 56° C. hot plate (Model 39D Hot Plate Analgesia Meter, IITC Inc., Woodland Hills, Calif.). The time (latency) until paw withdrawal was measured with a stopwatch. If the animal did not remove its paw from the hot plate within 12 seconds, it was removed by the experimenter to avoid injury to the animal or the development of hyperalgesia. The duration of thermal nociceptive block was calculated as the time required for thermal latency to return to a value of 7 seconds from a higher value. Seven seconds is the midpoint between a baseline thermal latency of approximately 2 seconds in adult rats, and a maximal latency of 12 seconds. Latencies greater than 7 sec were considered to be effective blocks.

Extensor Postural Thrust (EPT)

The rat was held with its posterior placed at a digital balance on which it could bear weight with one hindpaw at a time. The maximum weight that the rat could bear without its ankle touching the balance was measured.

Anesthetic

30 μM, 40 μM, or 50 μM TTX, 25 and 70 mM QX-314, and 70 and 100 mM QX-222 were tested alone or in combination for thermal nociceptor and motor blockade.

Results

Figure 5A:
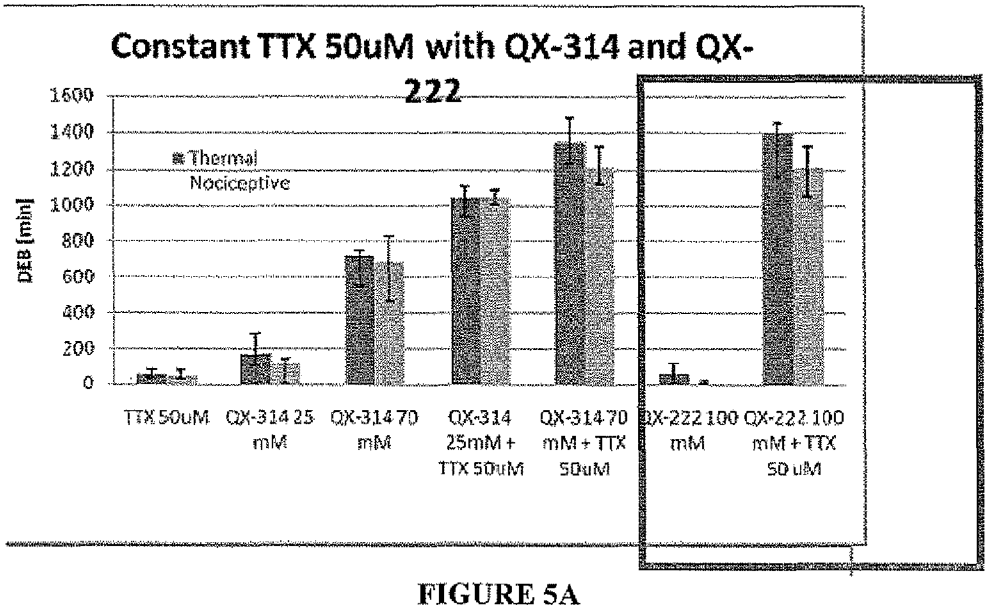
FIG. 5A is a graph of the effect of 50 μM TTX on the duration of effective motor (light grey) and thermal nociceptive (dark) block (minutes) from 100 mM QX-222 and 25 mM QX-314.
Figure 5B:
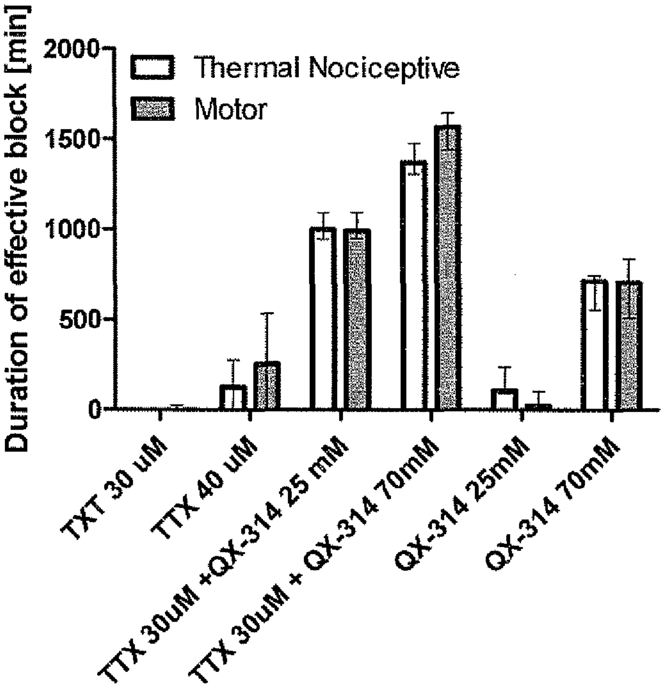
FIG. 5B is a graph of the effect of 30 and 40 μM TTX on the duration of effective motor (light grey) and thermal nociceptive (white) block (minutes) from 25 and 70 mM QX-314

The results are shown in FIGS. 5A and B. The combination of QX-314 or QX-222 with TTX increased blockade significantly more than the mere cumulative value of the anesthetics alone.

We claim:

1. A method for enhancing nerve blockade comprising administering an effective amount of a site I sodium channel local anesthetic selected from the group consisting of tetrodotoxin (TTX), saxitoxin (STX), decarbamoyl saxitoxin, neosaxitoxin, and gonyautoxins in combination with an effective amount of a chemical penetration enhancer selected from the group consisting of sodium octyl sulfate, sodium dodecyl sulfate, octyl-trimethyl-ammonium bromide, and dodecyl-trimethyl-ammonium bromide to increase duration of sensory nerve blockade more than the additive effect of the local anesthetic and chemical permeation enhancer.

2. The method of claim 1 wherein the local anesthetic is neosaxitoxin.

3. The method of claim 1 further comprising administering a vasoconstrictor.

4. The method of claim 1 further comprising a charged local anesthetic selected from the group consisting of amino-amide or amino-ester local anesthetics or derivatives thereof, at least partly amphiphilic local anesthetics, local anesthetics that act not on the surface of the ceil, and at least partly charged local anesthetics.

5. The method of claim 1 comprising providing a kit comprising a vial having the local anesthetic therein and a second vial containing a diluent therein.

6. The method of claim 1 comprising administering the anesthetic as a bolus dosage unit.

7. The method of claim 1 comprising administering the anesthetic in a continuous or sustained release formulation.

8. The method of claim 1 comprising administering the anesthetic in a topical or aerosol formulation.

9. An anesthetic composition for enhancing nerve blockade comprising an effective amount of a site I sodium channel local anesthetic selected from the group consisting of tetrodotoxin (TTX), saxitoxin (STX), decarbamoyl saxitoxin, neosaxitoxin, and gonyautoxins in combination with an effective amount of a chemical penetration enhancer selected from the group consisting of sodium octyl sulfate, sodium dodecyl sulfate, octyl-trimethyl-ammonium bromide, and dodecyl-trimethyl-ammonium bromide, to increase duration of sensory blockade more than the additive effect of the local anesthetic and chemical permeation enhancer.

10. The composition of claim 9 wherein the local anesthetic is neosaxitoxin.

11. The composition of claim 9 further comprising a vasoconstrictor.

12. The composition of claim 9 further comprising a charged local anesthetic selected from the group consisting of amino-amide or ambo-ester local anesthetics or derivatives thereof, at least partly amphiphilic local anesthetics, local anesthetics that act not on the surface of the cell, and at least partly charged local anesthetics.

13. The composition of claim 9 in a kit comprising a vial comprising the local anesthetic therein and a second vial comprising a diluent therein.

14. The composition of claim 9 comprising the anesthetic as a bolus dosage unit.

15. The composition of claim 9 comprising the anesthetic in a continuous or sustained release formulation.

16. The composition of claim 9 comprising the anesthetic in a topical or aerosol formulation.

17. The composition of claim 9 comprising a site I sodium channel local anesthetic selected from the group consisting of tetrodotoxin (TTX) in a concentration of between 10 and 120 micromolar, saxitoxin (STX) in a concentration of between 5 and 60 micromolar, decarbamoyl saxitoxin in a concentration between 30 and 480 micromolar, and neosaxitoxin in a concentration between 3 and 40 micromolar.

18. The composition of claim 9 comprising chemical penetration enhancer is selected from the group consisting of sodium octyl sulfate in a concentration of between 10 and 100 mM, sodium dodecyl sulfate in a concentration between one and 40 mM, octyl-trimethyl-ammonium bromide in a concentration of between 20 and 120 mM, and dodecyl-trimethyl-ammonium bromide in a concentration of between 0.5 and 10 mM.

19. The composition of claim 17 comprising chemical penetration enhancer is selected from the group consisting of sodium octyl sulfate in a concentration of between 10 and 100 mM, sodium dodecyl sulfate in a concentration between one and 40 mM, octyl-trimethyl-ammonium bromide in a concentration of between 20 and 120 mM, and dodecyl-trimethyl-ammonium bromide in a concentration of between 0.5 and 10 mM.

20. The composition of claim 12 wherein the local anesthetics has Formula I or Formula II:

Formula I

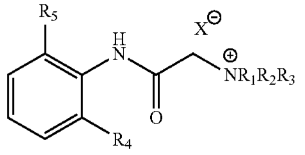

Formula II

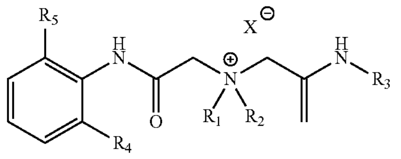

where $R_1$-$R_5$ are independently selected from hydrogen; linear, branched, or cyclic alkyl and aryl groups.

21. The composition of claim 20 wherein the local anesthetic is selected from the group consisting of QX-314 ((N-(2,6)dimethylphenylcarbamoylmethyl triethylammonium bromide); QX-222 (2-((2,6-dimethylphenyl)amino)-N,N,N-trimethyl-2-oxoethanaminium); QX-572 (N,N-bis(phenylcarbamoylmethyl)-dimethylammonium chloride), tonicaine, bupivacaine, charged tetracine derivatives, and charged derivatives of flecainide.

22. The composition of claim 9 wherein the effective amount of local anesthetic and effective amount of chemical penetration enhancer do not increase cytotoxicity.

23. The method of claim 1 wherein the effective amount of local anesthetic and effective amount of chemical penetration enhancer do not increase cytotoxicity.

* * * * *

UNITED STATES PATENT AND TRADEMARK OFFICE

CERTIFICATE OF CORRECTION

PATENT NO. : 8,658,699 B2
APPLICATION NO. : 12/993759
DATED : February 25, 2014
INVENTOR(S) : Kohane et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 231 days.

Signed and Sealed this
Twenty-ninth Day of September, 2015

Michelle K. Lee
*Director of the United States Patent and Trademark Office*